(12) United States Patent
Lord (10) Patent No.: US 10,477,893 B2
(45) Date of Patent: Nov. 19, 2019

(54) ELECTRONIC VAPOR PROVISION DEVICE

(71) Applicant: Nicoventures Holdings Limited, London (GB)

(72) Inventor: Christopher Lord, London (GB)

(73) Assignee: NICOVENTURES HOLDINGS LIMITED, London (GB)

( * ) Notice: Subject to any disclaimer, the term of this patent is extended or adjusted under 35 U.S.C. 154(b) by 0 days.

(21) Appl. No.: 14/401,511

(22) PCT Filed: May 14, 2013

(86) PCT No.: PCT/EP2013/059954
§ 371 (c)(1),
(2) Date: Nov. 14, 2014

(87) PCT Pub. No.: WO2013/171221
PCT Pub. Date: Nov. 21, 2013

(65) Prior Publication Data
US 2015/0136153 A1  May 21, 2015

(30) Foreign Application Priority Data

May 14, 2012 (GB) .................... 1208352.3

(51) Int. Cl.
*A24F 47/00* (2006.01)
*A61M 15/06* (2006.01)
(Continued)

(52) U.S. Cl.
CPC ......... *A24F 47/008* (2013.01); *A61M 11/042* (2014.02); *A61M 15/06* (2013.01);
(Continued)

(58) Field of Classification Search
USPC .............. 392/386–406; 128/200.11–207.18; 320/166–167
See application file for complete search history.

(56) References Cited

U.S. PATENT DOCUMENTS 2,057,353 A  10/1936 Whittemore, Jr.
4,947,875 A  8/1990 Brooks et al.
(Continued)

FOREIGN PATENT DOCUMENTS

CA  2641869 A1  5/2010
CN  1280661 A  1/2001
(Continued)

OTHER PUBLICATIONS

International Search Report and Written Opinion, mailed Sep. 25, 2013, for PCT/EP2013/059954, filed May 14, 2013.
(Continued)

*Primary Examiner* — Eric Yaary
(74) *Attorney, Agent, or Firm* — Patterson Thuente Pedersen, P.A.

(57) ABSTRACT

An electronic vapor provision device comprises a body 4 and a vaporizer 24. The body 4 comprises a power cell 10 and a processor 16, and the vaporizer 24 is releasably connectable to the body 4. The processor 16 is configured to enter a sleep mode when the vaporizer 24 is connected to the body 4 and the device is inactive for an inactive time. Furthermore, the processor 16 is configured to leave the sleep mode and enter a usable mode when the vaporizer 24 is disconnected from the body 4 then reconnected to the body 4.

10 Claims, 4 Drawing Sheets

(51) Int. Cl.
*A61M 11/04* (2006.01)
*A61M 16/00* (2006.01)

(52) U.S. Cl.
CPC ............. *A61M 2016/0021* (2013.01); *A61M 2016/0039* (2013.01); *A61M 2205/3653* (2013.01); *A61M 2205/8206* (2013.01)

(56) References Cited

U.S. PATENT DOCUMENTS

| | | | |
|---|---|---|---|
| 5,095,921 A * | 3/1992 | Losee et al. | 131/194 |
| 5,372,148 A * | 12/1994 | McCafferty et al. | 131/194 |
| 5,894,841 A * | 4/1999 | Voges | 128/203.12 |
| 5,949,632 A | 9/1999 | Barreras | |
| 6,040,560 A | 3/2000 | Fleischhauer | |
| 6,183,425 B1 | 2/2001 | Whalen | |
| 6,196,218 B1 | 3/2001 | Voges | |
| 6,958,691 B1 | 10/2005 | Anderson et al. | |
| 7,109,445 B2 | 9/2006 | Patterson | |
| 7,726,320 B2 | 6/2010 | Robinson et al. | |
| 8,550,069 B2 | 10/2013 | Alelov | |
| 8,997,753 B2 | 4/2015 | Li et al. | |
| 9,095,175 B2 | 8/2015 | Terry et al. | |
| 9,289,014 B2 | 3/2016 | Tucker et al. | |
| 9,439,455 B2 | 9/2016 | Alarcon | |
| 9,451,791 B2 | 9/2016 | Sears et al. | |
| 9,597,466 B2 | 3/2017 | Henry, Jr. et al. | |
| 2003/0033055 A1 | 2/2003 | McRae et al. | |
| 2003/0123328 A1 | 7/2003 | Guanter | |
| 2003/0123329 A1 | 7/2003 | Guanter | |
| 2003/0179003 A1* | 9/2003 | Toda et al. | 324/679 |
| 2003/0226837 A1 | 12/2003 | Blake et al. | |
| 2005/0045193 A1 | 1/2005 | Desmond | |
| 2005/0058441 A1* | 3/2005 | Kameyama et al. | 396/6 |
| 2005/0143866 A1 | 6/2005 | McRae | |
| 2005/0268911 A1 | 12/2005 | Cross et al. | |
| 2006/0047368 A1 | 3/2006 | Maharajh | |
| 2007/0045288 A1 | 3/2007 | Nelson | |
| 2008/0257367 A1 | 10/2008 | Paterno et al. | |
| 2009/0230117 A1 | 9/2009 | Fernando et al. | |
| 2009/0283103 A1 | 11/2009 | Nielsen | |
| 2010/0242974 A1 | 9/2010 | Pan | |
| 2011/0036346 A1 | 2/2011 | Cohen | |
| 2011/0113368 A1 | 5/2011 | Carvajal | |
| 2011/0210746 A1* | 9/2011 | Yugou et al. | 324/427 |
| 2011/0265806 A1 | 11/2011 | Alarcon et al. | |
| 2011/0304282 A1* | 12/2011 | Li et al. | 315/362 |
| 2012/0048266 A1 | 3/2012 | Alelov | |
| 2012/0060853 A1 | 3/2012 | Robinson | |
| 2012/0186594 A1 | 7/2012 | Liu | |
| 2012/0318882 A1* | 12/2012 | Abehasera | 239/1 |
| 2013/0042865 A1 | 2/2013 | Monsees | |
| 2013/0104916 A1 | 5/2013 | Bellinger | |
| 2013/0199528 A1 | 8/2013 | Goodman | |
| 2013/0228191 A1* | 9/2013 | Newton | A24F 47/008 131/329 |
| 2013/0255702 A1 | 10/2013 | Griffith, Jr. et al. | |
| 2013/0284192 A1 | 10/2013 | Peleg | |
| 2013/0319439 A1 | 12/2013 | Gorelick | |
| 2013/0340755 A1 | 12/2013 | Juster | |
| 2013/0340775 A1 | 12/2013 | Juster | |
| 2014/0123990 A1 | 5/2014 | Timmermans | |
| 2015/0114408 A1 | 4/2015 | Lord | |
| 2015/0128965 A1 | 5/2015 | Lord | |
| 2015/0128966 A1 | 5/2015 | Lord | |
| 2015/0136153 A1 | 5/2015 | Lord | |
| 2015/0237917 A1 | 8/2015 | Lord | |
| 2015/0245660 A1 | 9/2015 | Lord | |
| 2015/0257448 A1 | 9/2015 | Lord | |
| 2015/0336689 A1 | 11/2015 | Brown et al. | |
| 2016/0242466 A1 | 8/2016 | Lord et al. | |

FOREIGN PATENT DOCUMENTS

| | | |
|---|---|---|
| CN | 201029436 Y | 3/2008 |
| CN | 201238610 Y | 5/2009 |
| CN | 201393548 Y | 2/2010 |
| CN | 201821914 U | 5/2011 |
| CN | 201830899 U | 5/2011 |
| CN | 102934843 A | 2/2013 |
| CN | 202890466 U | 4/2013 |
| CN | 203070141 U | 7/2013 |
| CN | 103237468 A | 8/2013 |
| EP | 2404515 A1 | 1/2012 |
| EP | 2460423 A1 | 6/2012 |
| GB | 2468932 A | 9/2010 |
| GB | 2502053 A | 11/2013 |
| GB | 2502055 A | 11/2013 |
| GB | 2502162 A | 11/2013 |
| GB | 2502163 A | 11/2013 |
| GB | 2502164 A | 11/2013 |
| JP | H05212100 | 8/1993 |
| JP | 3392138 B2 | 1/2003 |
| JP | 2006-018057 | 1/2006 |
| JP | 2006-338178 | 12/2006 |
| KR | 20-2011-0002227 U | 3/2011 |
| RU | 72821 U1 | 5/2008 |
| RU | 2336001 C2 | 10/2008 |
| RU | 2336002 C2 | 10/2008 |
| RU | 94815 U1 | 6/2010 |
| RU | 2425608 C2 | 8/2011 |
| RU | 110608 U1 | 11/2011 |
| WO | WO 9418860 A1 | 9/1994 |
| WO | WO9501137 | 1/1995 |
| WO | WO 1998/017131 A1 | 4/1998 |
| WO | WO0064517 | 11/2000 |
| WO | WO2000064517 | 11/2000 |
| WO | WO 2004/080216 A1 | 9/2004 |
| WO | WO 2004/095955 A1 | 11/2004 |
| WO | 2009118085 A1 | 10/2009 |
| WO | WO2010073122 A1 | 7/2010 |
| WO | 2010091593 | 8/2010 |
| WO | 2010118644 A1 | 10/2010 |
| WO | WO 2010/145805 A1 | 12/2010 |
| WO | WO2011079932 A1 | 7/2011 |
| WO | 2011147699 A1 | 12/2011 |
| WO | WO2012048266 | 4/2012 |
| WO | WO 2012/109371 A2 | 8/2012 |
| WO | WO2012109371 A2 | 8/2012 |
| WO | WO 2013/060781 A1 | 5/2013 |
| WO | WO 2013/060784 A2 | 5/2013 |
| WO | WO2013060781 | 5/2013 |
| WO | WO 2013/098397 A2 | 7/2013 |
| WO | WO2013098398 | 7/2013 |
| WO | WO 2013/138384 A2 | 9/2013 |
| WO | WO 2014/037794 A2 | 3/2014 |
| WO | WO 2014/054035 A1 | 4/2014 |

OTHER PUBLICATIONS

Written Opinion, mailed Apr. 16, 2014, for PCT/EP2013/059954, filed May 14, 2013.
International Preliminary Report on Patentability, mailed Jul. 10, 2014, for PCT/EP2013/059954, filed May 14, 2013.
Chinese Office Action, Application No. 201380025370.4, mailed Mar. 21, 2016, 9 pages.
Vaishali et al., Random and Periodic Sleep Schedules for Target Detection in Sensor Networks, Journal of Computer Science and Technology, May 2008, 23(3) pp. 343-354.
Load Detecting Power Supply (National Semiconductor RD-166 Production Applications Design Center) Dec. 2008.
International Search Report and Written Opinion dated Apr. 2, 2014 for International Application No. PCT/EP2013/071070 filed Oct. 9, 2013.
International Preliminary Report on Patentability dated Nov. 21, 2014 for International Application No. PCT/EP2013/071070 filed Oct. 3, 2013.
Application and File History for U.S. Appl. No. 14/432,752, filed Mar. 31, 2015, inventor Christopher Lord.
PCT International Search Report and Written Opinion of the International Searching Authority for PCT/GB2014/053027, mailed Apr. 22, 2015, 13 pages.

(56) References Cited

OTHER PUBLICATIONS

PCT International Preliminary Report on Patentability for PCT/GB2014/053027, mailed Dec. 10, 2015, 19 pages.
Korean Office Action, Application No. 10-2014-7035205, dated Aug. 11, 2016, 6 pages.
Application and File History for U.S. Appl. No. 15/027,344 dated Apr. 5, 2016, Lord et al.
Japanese Notice of Reasons for Refusal for Japanese Application No. 2016520611 dated May 2, 2017. English translation provided.
Japanese Notice of Allowance, Japanese Application No. 2015-512037, dated Dec. 12, 2015, 3 pages.
Russian Decision of Grant, Russian Application No. 2014150496, dated Feb. 16, 2016, 7 pages.
Japanese Office Action, Application No. 2017-153826, dated Jun. 19, 2018, 3 pages (6 pages with translation).
Chinese Office Action, Application No. 201480055728.2, dated Nov. 17, 2017, 8 pages (20 pages with translation).
Russian Search Report, Application No. 2016147728, dated Mar. 27, 2018, 3 pages (6 pages with translation).
Korean Office Action, Application No. 2018-028946712, dated Apr. 27, 2018, 10 pages.
Canadian Office Action, Application No. 2,997,062, dated Mar. 4, 2018, 6 pages.
Japanese Office Action, Application No. 2018-033546, dated Feb. 15, 2019, 5 pages (12 pages with translation).
Application and File History for U.S. Appl. No. 16/188,862, filed Nov. 13, 2018, Inventor: Lord et al.
Korean Office Action, Application No. 10-2018-7014831, dated Dec. 28, 2018, 8 pages (15 pages with translation).
Japanese Search Report for Application No. 2016-520611, dated Mar. 28, 2017 (17 pgs.) and English Machine Translation (28 pgs.) (46 pgs. total).
Korean Office Action for Application No. 10-2016-7009422, dated Jul. 26, 2017 (9 pgs.) and English Translation (8 pgs.) (17 pgs. total).
Russian Decision to Grant for Application No. 122987, dated Apr. 29, 2016 (12 pgs).

* cited by examiner

ELECTRONIC VAPOR PROVISION DEVICE

CLAIM FOR PRIORITY

This application is the National Stage of International Application No. PCT/EP2013/059954, filed May 14, 2013, which in turn claims priority to and benefit of British Patent Application No. GB1208352.3, filed May 14, 2012. The entire contents of the aforementioned applications are herein expressly incorporated by reference.

FIELD

The specification relates to electronic vapour provision devices. More particularly, but not exclusively, the specification concerns electronic vapour provision devices in the form of electronic cigarettes.

BACKGROUND

Electronic vapour provision devices are typically cigarette-sized and function by allowing a user to inhale a nicotine vapour from a liquid store by applying a suction force to a mouthpiece. Some electronic vapour provision devices have an airflow sensor that activates when a user applies the suction force and causes a heater coil to heat up and vaporise the liquid. Electronic vapour provision devices include electronic cigarettes.

SUMMARY

In an embodiment there is provided an electronic vapour provision device comprising a body and a vaporiser, wherein the body comprises a power cell and a processor; the vaporiser is releasably connectable to the body; the processor is configured to enter a sleep mode when the vaporiser is connected to the body and the device is inactive for an inactive time; and the processor is configured to leave the sleep mode and enter a usable mode when the vaporiser is disconnected from the body then reconnected to the body.

This has the advantage that once the device has entered a sleep mode, it does not accidentally enter a normal mode. Entering a normal mode requires effort from the user.

The electronic vapour provision device may be an electronic cigarette.

The sleep mode can be a low power mode. Moreover, the sleep mode may be the lowest non-zero power mode of the device.

By remaining in a low power sleep mode the device remains active yet consumes very little power. This provides an efficient use of power and minimises energy wastage.

The device has a further advantage that it can remain in a low power mode without the additional use of a switch to deactivate and activate.

Furthermore, the electronic vapour provision device can use less power in sleep mode than in usable mode.

Advantageously, the usable mode is a higher power state to enable a more rapid activation once the device is activated by a user.

The electronic vapour provision device may be inactive when not being used as a vapour provision device by a user.

The body may further comprise a capacitor; and the processor can be configured to first charge the capacitor and then detect whether the vaporiser is connected to the body by determining whether the capacitor is discharged.

The body may comprise first and second body connection terminals, and the vaporiser may comprise first and second vaporiser connection terminals. Furthermore, the device may be configured such that when the vaporiser is connected to the body, the first body connection terminal is connected to the first vaporiser connection terminal and the second body connection terminal is connected to the second vaporiser connection terminal.

The capacitor can be connected in parallel with the first and second body connection terminals. The computer can be configured to send out a pulse and the capacitor can be charged for a period of time equal to the width of the pulse. Moreover, the pulse may be a square wave.

In another embodiment there is provided the vaporiser of the electronic vapour provision device of other embodiments.

In another embodiment there is provided the an electronic vapour provision device body, comprising a power cell and a processor, and configured to be releasably connectable to a vaporiser; wherein the processor is configured to enter a sleep mode when the vaporiser is connected to the body and the device is inactive for an inactive time; and the processor is configured to leave the sleep mode and enter a usable mode when the vaporiser is disconnected from the body then reconnected to the body.

In another embodiment there is provided an electronic smoking device comprising a battery assembly and a vaporiser, where the battery assembly comprises a power cell and a computer, the vaporiser is releasably-attachable to the battery assembly and the computer comprises a computer processor, a memory and an input-output means; wherein when the vaporiser is attached to the battery assembly, the computer is configured in use to enter a sleep mode when the device is inactive for a predetermined inactive time.

In another embodiment there is provided a method of triggering a change in the mode of a processor of an electronic vapour provision device from a sleep mode to a usable mode, wherein the electronic vapour provision device comprises a body and a vaporiser; the body comprises a power cell and the processor; and the vaporiser is releasably connectable to the body; the method comprising disconnecting the vaporiser from the body and then reconnecting the vaporiser to the body.

As used herein, the term vapour includes an aerosol and other fluid streams for provision to a user by the electronic vapour provision device.

BRIEF DESCRIPTION OF THE DRAWINGS

For a better understanding of the disclosure, and to show how example embodiments may be carried into effect, reference will now be made to the accompanying drawings in which.

DETAILED DESCRIPTION

Figure 1:
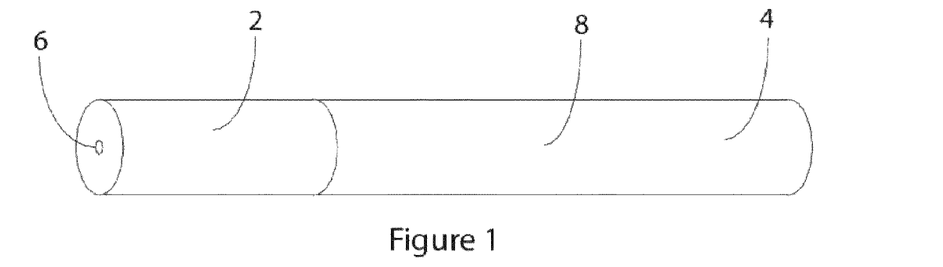
FIG. 1 is a side perspective view of an electronic vapour provision device.
Figure 2:
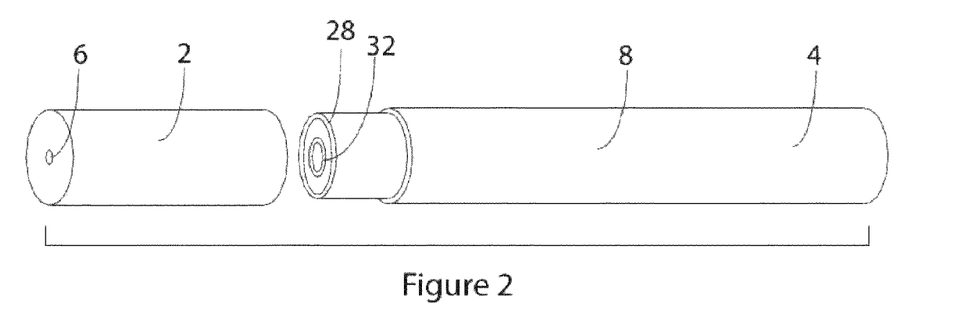
FIG. 2 is an exploded side perspective view of the electronic vapour provision device of FIG. 1.
Figure 3:
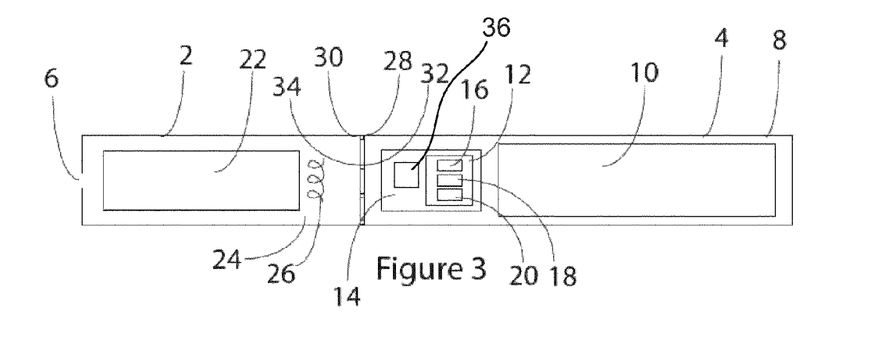
FIG. 3 is a side sectional view through the device of FIG. 1.

Referring to FIGS. 1 to 3 there is shown an electronic vapour provision device, also herein referred to as an electronic smoking device, that comprises a mouthpiece 2 and a body 4. The electronic vapour provision device is shaped like a conventional cigarette, both the mouthpiece 2 and body 4 are cylindrical and are configured to connect to each other coaxially so as to form the conventional cigarette shape. The mouthpiece 2 is connectable to the body 4 at a first end of the mouthpiece 2 and has an air outlet 6 at a second end. The body 2 comprises a battery assembly 8, comprising a power cell 10 and a computer 12 on a circuit board 14, wherein the power cell 10 is connected to the computer 12. The computer 12 comprises a computer processor 16, a memory 18 and input-output arrangement 20. In this example the computer 12 is a microcontroller. The computer 12 is configured to control and interface with the other electrical components of the battery assembly 8, comprising the power cell 10, via the input-output arrangement 20.

The mouthpiece 2 comprises a liquid bottle 22 and a vaporiser 24 having a heater coil 26. For example, the vaporiser 24 is in fluid communication with the liquid bottle 22. The mouthpiece 2 is connectable to the battery assembly 8 by a screw thread, wherein connection of the battery assembly 8 and the mouthpiece 2 connects a first battery assembly terminal 28 to a first vaporiser terminal 30 and a second battery assembly terminal 32 to a second vaporiser terminal 34, forming an electrically conductive contact in both cases. The vaporiser terminals 30 34 are electrically connected in parallel to the heater coil 26 of the vaporiser 24.

The herein described configuration of the computer 12 comprises the computer operating according to a computer program stored in its memory 18 and accessed by its computer processor 16.

The device is configured such that, if the computer determines that the vaporiser 24 is connected to the battery assembly 8, then the computer 12 initially remains in a normal operation mode.

Moreover, to maximise the lifetime of the charge in the power cell 10, the device is configured such that, if the computer 12 determines that the vaporiser 24 is not connected to the battery assembly 8, then the computer 12 enters a low power sleep mode.

Furthermore, to maximise the lifetime of the charge in the power cell 10 while the computer 12 determines that the vaporiser 24 is connected, the computer 12 is configured to detect when the device has been inactive for a predetermined inactive time such as 12 minutes. This inactive time is the time that has elapsed since use of the device by the user. Moreover, in response to detecting that the device has been inactive for the inactive time, the computer 12 is configured to leave normal operational mode and to enter a low power sleep mode. For example, sleep mode may comprise the computer 12 consuming minimal power and performing no processing. A period during which the computer 12 is in sleep mode is herein referred to as sleep time. Furthermore, the device is configured such that, in order to return the device to a normal operational mode, a user is required to disconnect the vaporiser 24 from the battery assembly 8 and then reconnect the vaporiser 24 to the battery assembly 8. This configuration of the device comprises the computer 12 being configured to detect when the vaporiser 24 has been disconnected and then reconnected to the battery assembly 8. Moreover, in response to detection by the computer 12 of disconnection and reconnection of the vaporiser 24, the computer 12 is configured to leave sleep mode and re-enter the normal operation mode.

The computer 12 determining whether the vaporiser 24 is connected to the battery assembly 8 and/or detecting whether the vaporiser 24 has been disconnected and then reconnected may for example comprise the computer 12 periodically checking whether the vaporiser 24 is connected to the battery assembly 8 during both normal operation mode and sleep mode.

For example, after determining that the vaporiser 24 is not attached and entering sleep mode, the computer 12 may then remain in sleep mode for an initial sleep time of two seconds. After the sleep time, the computer 12 wakes and immediately and quickly checks again for a vaporiser connection. Again, if the vaporiser 24 is not connected the computer 12 goes into sleep mode for another two seconds. The time that the computer 12 is awake is extremely short compared to the sleep time so the circuit remains predominantly in a low power mode, thus conserving power. During the sleep time no checks are made to determine whether the vaporiser 24 is attached however a user may take several seconds to assembly the device, connecting the vaporiser 24 and the battery assembly 8, so the vaporiser 24 connection may be easily established by the computer 12 before use of the device by a user.

Furthermore, after determining that the vaporiser 24 is connected and that the device has been inactive in this connected state for the inactive time and then entering sleep mode, the computer 12 may then remain in sleep mode for an initial sleep time of two seconds. After the sleep time, the computer 12 wakes and immediately and quickly checks again for a vaporiser connection. Again, if the vaporiser is still connected the computer 12 goes into sleep mode for another two seconds. The time that the computer 12 is awake is extremely short compared to the sleep time so the circuit remains predominantly in a low power mode, thus conserving power. During the sleep time no checks are made to determine whether the vaporiser 24 is attached. However a user may take several seconds to disconnect the vaporiser 24 and several seconds to then reconnect the vaporiser 24, so the computer 12 may easily detect and log the disconnection and subsequent reconnection. In this way the computer 12 is able to detect the disconnection and subsequent reconnection of the vaporiser 24 by a user and to respond accordingly by leaving sleep mode and entering normal operation mode.

The waking of the computer 12 may for example comprise the computer 12 entering a waking mode distinct from the sleep mode and the normal operation mode.

The computer 12 checking whether the vaporiser 24 is connected to the battery assembly 8 may for example comprise the computer 12 sending an electrical pulse to the battery assembly terminals 28, 32. For example, the computer 12 may control the power cell 10 so as to supply a pulse of current to the first battery assembly terminal 28 and may measure the current reaching the second the battery assembly terminal 32, for example using a digital multimeter of the battery assembly 8. The digital multimeter is referenced 44 in the circuit diagram of FIG. 8. Furthermore, if the vaporiser 24 is connected, the digital multimeter reads a current reaching the second battery assembly terminal 32 via the vaporiser 24 and provides information to the computer 12 indicating this.

The battery assembly 8 of the electronic cigarettes described herein further comprises an air pressure sensor 36, wherein the air pressure sensor is powered by the power cell 10 and controlled by the computer 12. Once the vaporiser is connected to the battery assembly 8, and while the device is still in the normal operation mode resulting from the processors detection of this connection, in order to use the device the user must suck on the mouthpiece 2. The electronic cigarette is configured such that the user sucking on the mouthpiece 2 causes a drop in air pressure at the air pressure sensor 36. The computer 12 therefore receives information from the air pressure sensor 36 indicating that a user is sucking on the device. In response to this information, the computer 12 controls the power cell 10 to power the vaporiser 24. For example, the computer may control the power cell 10 to power the vaporiser 24 via the respective first and second terminals of both the battery assembly and the vaporiser. This causes the vaporisation of liquid communicated to the vaporiser 24 from the liquid bottle 22. Consequently, use of the device by a user comprises the user sucking on the device and the detection of this user interaction by the device so as to trigger the vaporisation of the liquid contained in the device. The provided vapour then passes to the user. The vapour provision device is configured such that a user can only use the device, by sucking on the mouthpiece 2, when the computer is in the normal operation mode. The normal operation mode can therefore be described as a usable mode.

Figure 4:
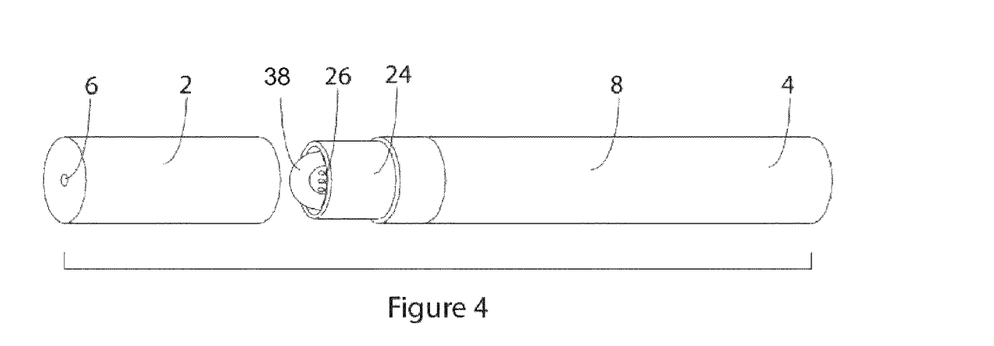
FIG. 4 is a side perspective view of an electronic vapour provision device with separated mouthpiece and body.
Figure 5:
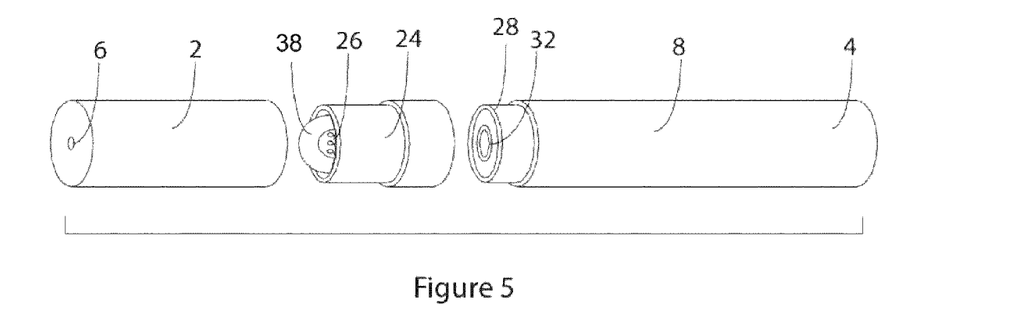
FIG. 5 is a side perspective view of an electronic vapour provision device with separated mouthpiece, vaporiser and battery assembly.
Figure 6:
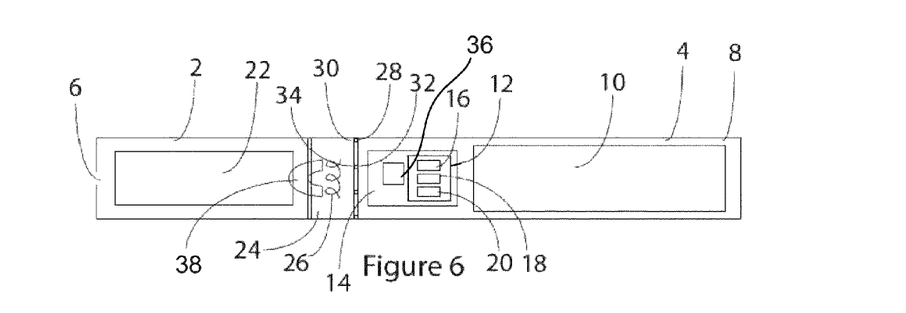
FIG. 6 is a side sectional view through the electronic vapour provision device of FIG. 4 with connected mouthpiece and body.

FIGS. 4 to 6 show another example of an electronic vapour provision device. This device is similar to that shown in FIGS. 1 to 3. However in this example the vaporiser 24 does not form part of the mouthpiece 2. The mouthpiece 2 contains a liquid bottle 22 and is attachable to the vaporiser 24. The vaporiser 24 has a heater coil 26 and additionally a wick 38. For example the wick 38 may be a mesh wick. The mouthpiece 2 and the vaporiser 24 are configured to connect to each other such that the wick 38 acts to communicate liquid from the liquid container 22 onto the vaporiser 24. The configuration of the device involving the conservation of power based on interaction between the vaporiser 24 and the battery assembly 8 involving the disconnection and reconnection of the vaporiser is as described above.

Figure 7:
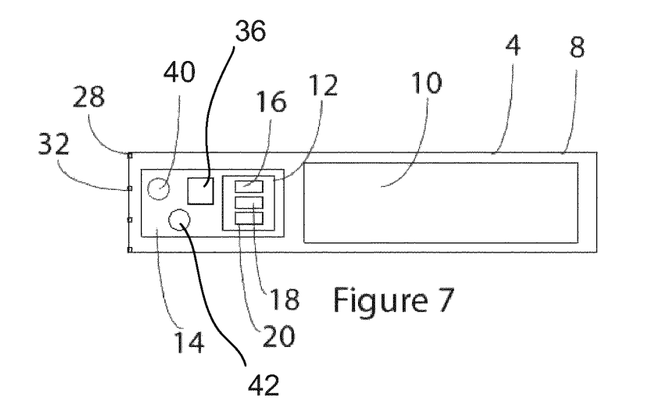
FIG. 7 is a side sectional view of a battery assembly having a capacitor.
Figure 8:
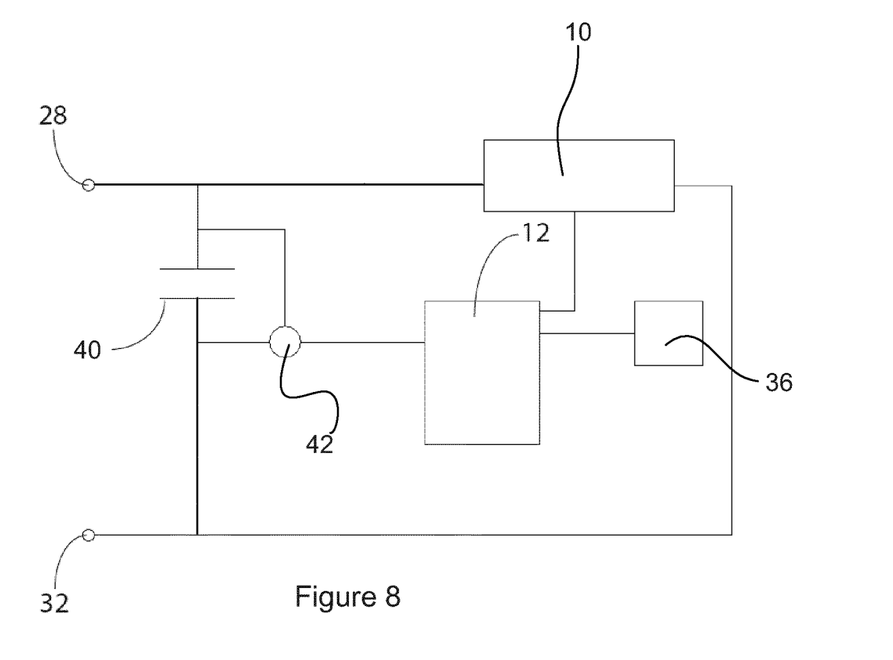
FIG. 8 is a circuit diagram for the battery assembly of FIG. 7.

A further example of how, in the cigarettes of FIGS. 1 to 6, connection of the vaporiser 24 to the body may be detected by the computer 12 is now described with reference to FIGS. 7 and 8. With respect to FIGS. 7 and 8, the battery assembly 8 of the electronic vapour provision device is similar to that shown in FIG. 1 to FIG. 6, additionally comprising a capacitor 40 and a digital multimeter 42. The capacitor 38 is arranged in a circuit such that it is in parallel to the battery assembly terminals and to the power cell 10. The digital multimeter 42 of the battery assembly 8 is wired in a switched parallel circuit to the capacitor 40. To test whether the vaporiser 24 is connected to the battery assembly 8, the computer 12 first controls the power cell to charge the capacitor 40, then waits a short time and checks the charge of the capacitor 40. The computer 12 checks the charge of the capacitor 40 by triggering the completion of the switched digital multimeter circuit and then receives information from the multimeter 42 indicating a voltage across the capacitor 40 resulting from the charge of the capacitor 40. If the vaporiser 24 is connected, the resistance of the vaporiser 24 causes the capacitor 40 to discharge quickly so the computer 12 measures at least a substantially fully discharged capacitor 40. If the vaporiser 24 is not connected the capacitor 40 is not substantially fully discharged when checked by the computer 12.

With regard to the embodiments described herein, the following alternatives and variations will now be described.

The electronic vapour provision devices described may be electronic cigarettes. However, the device is not restricted to being cigarette shaped.

The sleep time may be substantially 2 seconds. However, the sleep time is not restricted to 2 seconds and other suitable values could be used. Moreover, the time between entering sleep modes can be significantly less than the sleep time.

The computer processor 16 can be a microprocessor. Moreover, the computer 12 may comprise a microcontroller. Furthermore, a computer such as a microcontroller could utilise a watchdog timer to implement the sleep time wait in the low power mode. Using a microcontroller has space saving advantages since the entire computer is located on a single chip and therefore the size of the device is minimised. Fewer components to assemble also provides reduced manufacturing times are costs. The computer is not restricted being a microcontroller and could be fabricated from separate processor, memory and input-output components.

The vaporisers 24 described are examples only.

Moreover, the sleep mode may be the lowest non-zero power mode of the device.

Although an air pressure sensor 36 is described, other configurations may be employed to detect when a user is attempting to use the device. For example, an airflow sensor may be used and the device may be configured such that sucking on the mouthpiece 2 by a user causes a flow of air past the airflow sensor.

Although a liquid bottle 22 is described, other types of liquid storage may be used. For example the device may comprise foam partially saturated in liquid for vaporisation.

Although a digital multimeter 42 is described as being used by the computer 12 to determine the level of charge of the capacitor 40, other suitable configurations may be employed for this purpose. For example, a digital voltmeter may instead be used.

The electronic vapour provision devices are described as being configured such that the computer 12 can determine when the vaporiser 24 is connected to the battery assembly 8 of the body 4. This configuration of the electronic vapour provision device may be described as the device comprising a sensor arrangement configured to detect when the vaporiser is connected and to provide information to the processor accordingly. For example, with regard to the device of FIGS. 7 and 8, the first and second battery assembly terminals 28 32, the capacitor 40 and the digital multimeter 42 may together be considered as a sensor arrangement of the device. In this sense, the sensor arrangement may take other forms to that described. For example, the sensor arrangement may comprise only one sensor, for instance a pressure sensor configured to detect a mechanical pressure resulting from connection of the vaporiser 24 to the body 4.

The various embodiments described above facilitate a number of improvements.

The described configuration of the electronic vapour provision device is such that in the case of the vaporiser 24 being connected and the device entering the sleep mode due to the device being inactive for the inactive time, the device can not then accidentally enter a normal mode. Moreover, a user must be aware of the requirement to disconnect and then reconnect the vaporiser 24 and must carry this procedure out in order to trigger the device to enter the usable, normal operation mode. Entering a normal mode requires effort from the user. This facilitates the advantage of increased safety and control of use of the device.

Described operational modes and configurations of the computer may be operational modes and configurations of the processor.

Although examples have been shown and described it will be appreciated by those skilled in the art that various changes and modifications might be made without departing from the scope of the invention.

In order to address various issues and advance the art, the entirety of this disclosure shows by way of illustration various embodiments in which the claimed invention(s) may be practiced and provide for superior electronic vapour provision devices. The advantages and features of the disclosure are of a representative sample of embodiments only, and are not exhaustive and/or exclusive. They are presented only to assist in understanding and teach the claimed features. It is to be understood that advantages, embodiments, examples, functions, features, structures, and/or other aspects of the disclosure are not to be considered limitations on the disclosure as defined by the claims or limitations on equivalents to the claims, and that other embodiments may be utilised and modifications may be made without departing from the scope and/or spirit of the disclosure. Various embodiments may suitably comprise, consist of, or consist essentially of, various combinations of the disclosed elements, components, features, parts, steps, means, etc. In addition, the disclosure includes other inventions not presently claimed, but which may be claimed in future. Any feature of any embodiment can be used independently of, or in combination with, any other feature.

The invention claimed is:

1. An electronic vapor provision device comprising:
   a body including a power cell and a processor, wherein the processor has a normal operation mode and a lower power sleep mode; and
   a mouthpiece comprising a liquid store and a vaporizer, wherein the vaporizer is in fluid communication with the liquid store using a wick to transport liquid from the liquid store to the vaporizer for vaporization,
   wherein the mouthpiece is connectable to the body in a co-axial manner, and
   wherein the processor is configured to:
      periodically check, during both the normal operation mode and the lower power sleep mode, whether the mouthpiece is connected to or disconnected from the body,
      detect when the device has been inactive for a predetermined inactive time while the mouthpiece is connected to the body,
      in response to such a detection of the device being inactive, and while the mouthpiece is connected to the body, transition from the normal operation mode into the lower power sleep mode,
      detect, based on the periodic checking, and after the transition from the normal operation mode to the lower power sleep mode, that the mouthpiece has been disconnected from the body,
      detect, based on the periodic checking, after the mouthpiece has been disconnected from the body, that the mouthpiece has been reconnected to the body, and
      in response to such a detection of the disconnection and then reconnection, transition from the lower power sleep mode back into the normal operation mode.

2. The electronic vapor provision device of claim 1, wherein the electronic vapor provision device is an electronic cigarette.

3. The electronic vapor provision device of claim 1, wherein the lower power sleep mode is a lowest non-zero power mode of the device.

4. The electronic vapor provision device of claim 1, wherein the electronic vapor provision device is inactive when not being used as a vapor provision device by a user.

5. The electronic vapor provision device of claim 1, wherein the body comprises first and second body connection terminals, and the vaporizer comprises first and second vaporizer connection terminals,
   the device configured such that when the vaporizer is connected to the body, the first body connection terminal is connected to the first vaporizer connection terminal and the second body connection terminal is connected to the second vaporizer connection terminal.

6. The electronic vapor provision device of claim 5, wherein:
   the body further includes a capacitor; and
   the processor is further configured to first charge the capacitor and then detect whether the vaporizer is connected to the body by determining whether the capacitor is substantially discharged.

7. The electronic vapor provision device of claim 6, wherein the capacitor is connected in parallel with the first and second body connection terminals.

8. The electronic vapor provision device of claim 6, further comprising a computer configured to send out a pulse and charge the capacitor for a period of time substantially equal to the width of the pulse.

9. The electronic vapor provision device of claim 8, wherein the pulse is a square wave.

10. A processor-implemented method of triggering a change, in the mode of a processor of an electronic vapor provision device, from a lower power sleep mode to a normal operation mode, wherein the electronic vapor provision device comprises a body comprising a power cell and the processor, and a mouthpiece comprising a liquid store and a vaporizer, wherein the vaporizer is in fluid communication with the liquid store using a wick to transport liquid from the liquid store to the vaporizer for vaporization, and the mouthpiece is connectable to the body in a co-axial manner, the method comprising:
   periodically checking, during both the normal operation mode and the lower power sleep mode, whether the mouthpiece is connected to or disconnected from the body;
   detecting when the device has been inactive for a predetermined inactive time while the mouthpiece is connected to the body;
   in response to such a detection of the device being inactive, and while the mouthpiece is connected to the body, transitioning from the normal operation mode into the lower power sleep mode;
   detecting, based on the periodic checking, and after the transition from the normal operation mode into the lower power sleep mode, that the mouthpiece has been disconnected from the body;
   detecting, based on the periodic checking, after the mouthpiece has been disconnected from the body, that the mouthpiece has been reconnected to the body; and
   in response to such a detection of the disconnection and then reconnection, transitioning from the lower power sleep mode back into the normal operation mode.

* * * * *